(12) United States Patent
Li

(10) Patent No.: US 9,554,938 B2
(45) Date of Patent: Jan. 31, 2017

(54) ANTI-SNORING DEVICE

(76) Inventor: Wu Li, München (DE)

(*) Notice: Subject to any disclaimer, the term of this patent is extended or adjusted under 35 U.S.C. 154(b) by 508 days.

(21) Appl. No.: 12/990,670

(22) PCT Filed: Apr. 29, 2009

(86) PCT No.: PCT/DE2009/000614
§ 371 (c)(1),
(2), (4) Date: Nov. 2, 2010

(87) PCT Pub. No.: WO2009/132640
PCT Pub. Date: Nov. 5, 2009

(65) Prior Publication Data
US 2011/0048431 A1 Mar. 3, 2011

(30) Foreign Application Priority Data

May 2, 2008 (DE) .................... 20 2008 006 076 U

(51) Int. Cl.
*A61F 5/56* (2006.01)
(52) U.S. Cl.
CPC ..................................... *A61F 5/566* (2013.01)
(58) Field of Classification Search
USPC .................. 128/859–862; 602/902; 433/6–7; 606/234–236
See application file for complete search history.

(56) References Cited

U.S. PATENT DOCUMENTS

| | | | | |
|---|---|---|---|---|
| 3,682,164 A * | 8/1972 | Miller | ............................ | 128/857 |
| 5,092,346 A | 3/1992 | Hays et al. | | |
| 5,133,740 A * | 7/1992 | Kussick | ......................... | 606/236 |
| 5,154,184 A * | 10/1992 | Alvarez | ......................... | 128/848 |
| 5,752,822 A * | 5/1998 | Robson | .................... | A61F 5/566 |
| | | | | 128/860 |
| 5,876,199 A * | 3/1999 | Bergersen | ................ | A61C 7/08 |
| | | | | 433/6 |
| 5,988,170 A | 11/1999 | Thomas | | |
| 6,494,209 B2 * | 12/2002 | Kulick | ........................... | 128/848 |
| 6,675,804 B1 * | 1/2004 | Pivovarov | ..................... | 128/848 |
| 6,773,451 B1 * | 8/2004 | Dussere | .................. | A61J 17/00 |
| | | | | 606/235 |
| 6,837,246 B1 * | 1/2005 | DeLuke | .................. | A61F 5/566 |
| | | | | 128/860 |
| 6,976,491 B2 * | 12/2005 | D'Agosto | ..................... | 128/859 |

(Continued)

FOREIGN PATENT DOCUMENTS

DE 40 26 602 C1 11/1991
EP 0 312 368 B1 4/1989
(Continued)

*Primary Examiner* — Ophelia A Hawthorne
(74) *Attorney, Agent, or Firm* — Fitch, Even, Tabin & Flannery LLP

(57) ABSTRACT

An anti-snoring device for positioning within the mouth cavity of a person is disclosed. The invention is characterized in that a displacement member (9) is provided with a shape and size suitable for placement within the mouth cavity between the bottom of the tongue and the musculature at the bottom of the mouth, the member lifting the tongue in toward the mouth cavity, wherein the displacement member is connected to a mouthpiece-shaped element (8) placed between the teeth of the upper and lower jaw, and provides a passage opening (15) for ventilation of the mouth cavity with air that is breathed.

21 Claims, 3 Drawing Sheets

(56) References Cited

U.S. PATENT DOCUMENTS

| | | | |
|---|---|---|---|
| 7,029,491 B2* | 4/2006 | Davis | A61J 17/00 606/234 |
| 7,533,674 B2* | 5/2009 | Dort | 128/859 |
| 2004/0059382 A1* | 3/2004 | Bergersen | 606/234 |
| 2005/0166929 A1* | 8/2005 | Jiang | A61F 5/566 128/861 |
| 2009/0188510 A1* | 7/2009 | Palmer | 128/848 |

FOREIGN PATENT DOCUMENTS

| | | |
|---|---|---|
| EP | 0 599 445 A1 | 6/1994 |
| GB | 874 480 A | 8/1961 |
| WO | WO 92/05752 | 4/1992 |
| WO | WO 92/09249 | 6/1992 |

\* cited by examiner

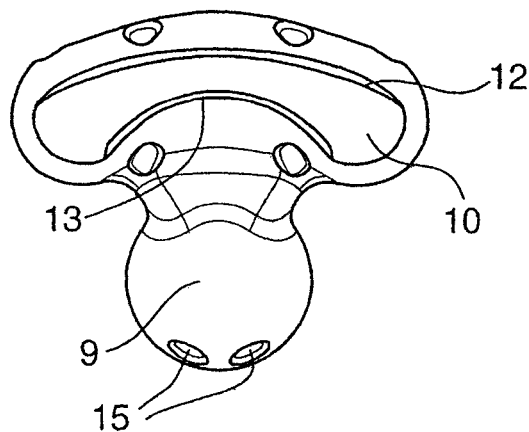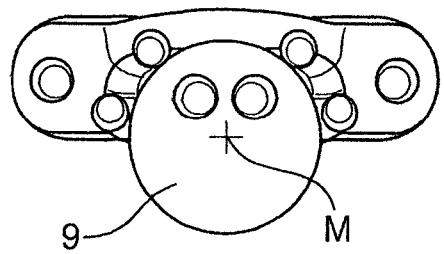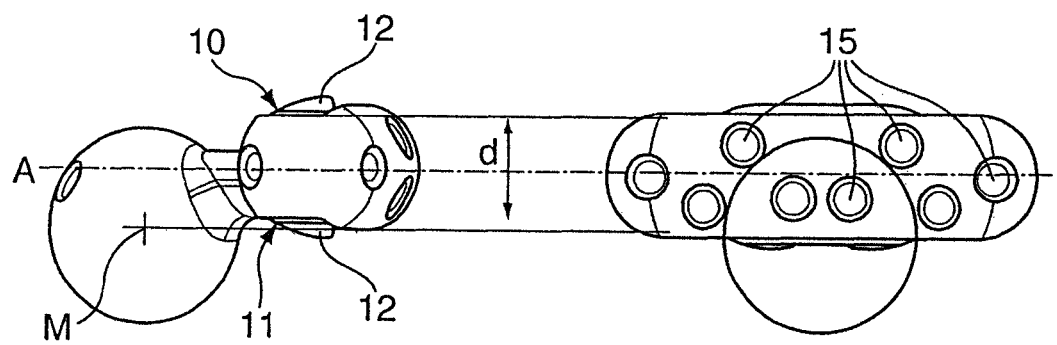
Fig. 4a  Fig. 4b
Fig. 4c  Fig. 4d
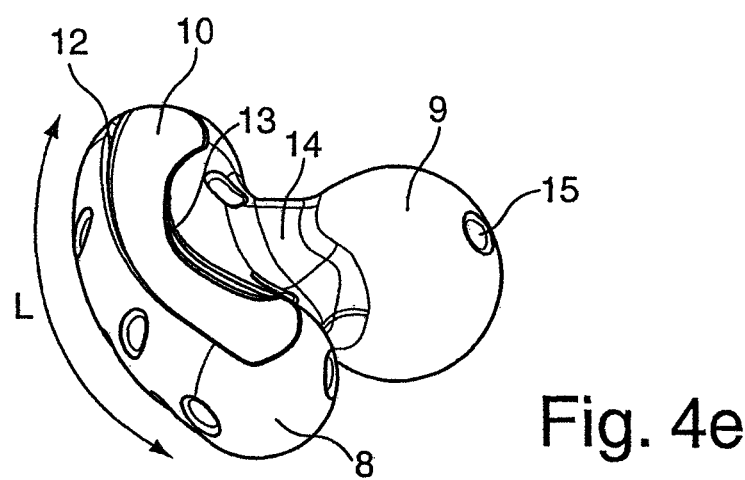
Fig. 4e

ANTI-SNORING DEVICE

BACKGROUND OF THE INVENTION

Field of the Invention

The invention relates to an anti-snoring device for positioning within the mouth cavity of a person.

Description of the Prior Art

The noise made during breathing when asleep (snoring) is, in particular, very disruptive for people in the vicinity of the snorer. In addition, snoring may even pose a risk to the health of the snorer, for example in the case of obstructive sleep apnoea. Snoring is generally produced by weak muscle tone of the neck muscles during sleep. The airways become narrowed until they close completely (apnoea). This leads to an increased air flow and to the generation of noise by the structures that droop during movement. Muscle tension naturally decreases in older individuals in the throat region, which is why this group of people snore more often than younger individuals.

A wide range of devices, aids and breathing masks to prevent snoring are known, including surgical procedures.

Operations generally remove the structures preventing breathing, such as enlarged tonsils, polyps, etc. However, the success rate with regard to snoring varies very widely from 20-40%. According to many reports the relapse rate is very high.

A breathing mask provides continuous positive airway pressure and therefore holds the airways open. Since it is a very expensive and complex piece of equipment that is uncomfortable for the snorer, it is primarily indicated in severe cases of apnoea.

Intraoral devices are worn at night and generally displace the lower jaw in a forward direction so as to open the pharyngeal portion of the airways. The base of the tongue is also entrained with the lower jaw in a forward direction, thus making it possible to open the airways. Success can be achieved using these devices, but they are usually found to be very cumbersome by the wearer as a result of their construction and design.

Known oral anti-snoring devices representative of a large number of known generic devices can be inferred from the following documents:

DE 40 26 602 C1 discloses a device for preventing snoring comprising a prosthesis part that is fixed to the teeth and to which a bow is attached via a spring mechanism in such a way that, on the one hand, the tongue is pressed away from the posterior soft palate and, on the other hand, the tongue can be pressed against the palate during swallowing.

EP 0 312 368 B1 discloses a modified mouthpiece as an anti-snoring device, onto which the teeth of the upper jaw bite, a lower sliding connecting member pressing the mouthpiece toward the mouth cavity opening against the inner faces of the teeth of the lower jaw, whereby the lower jaw is pushed forward and the distance between the tongue and the soft palate is enlarged.

EP 0 254 918 A1 discloses an upper and lower jaw plate comprising inserted magnets that hold both jaws at a specific distance by opposed magnetic repulsion.

DE 27 04 709 A1 represents a normal gag.

EP 0 599 445 A1 discloses a device with rigid fixing of the upper jaw and loose fixing of the lower jaw. The oral side of the device is configured in such a way that the tongue can be placed in a sucking position.

WO 92/05752 discloses a device comprising a palate plate and a mouth base plate that simultaneously push the lower jaw forward and force the wearer to breathe through their nose. Two variants are disclosed: one in which the device is fixed to the teeth, and one in which the device sits freely in the mouth.

WO 92/09249 discloses a device for preventing tongue thrust, teeth grinding and snoring. Adapted to the tongue and teeth, the device holds the tongue forward by suction.

U.S. Pat. No. 5,092,346 discloses a device for the upper jaw comprising a ramp for the lower jaw to push the lower jaw forward, and a breathing opening between the upper jaw part and the lower jaw ramp.

DE 23 20 501 C3 discloses a device that is similarly constructed to an orthodontic activator and comprises an additional labial and adjustable lip shield. The lower jaw is pushed forward by muscle activity and corresponding grinding guides in the device for the teeth. However, the muscles still droop during sleep and muscle tone is decreased or cancelled out completely.

The main drawback of known devices is that the devices are decidedly uncomfortable to wear owing to their voluminous expansion, their constraints caused by a bite guard, their pressure on the tongue or soft palate parts, and the restricted freedom of movement of the lower jaw and tongue. The feeling of a large, annoying foreign body in the mouth prevents the snorer from falling asleep, which generally leads to the devices not being used.

SUMMARY OF THE INVENTION

The invention is an anti-snoring device that makes it possible to overcome the above drawbacks. In particular, the invention is an anti-snoring device which is worn orally allowing the wearer to obtain the required depth of sleep and feeling of well-being, in particular as a result of the low expansion in the jaw region and the high level of comfort when wearing the anti-snoring device.

In accordance with the invention, an anti-snoring device adapted for positioning within the mouth cavity of a person includes a displacement member provided with a shape and size suitable for placement within the mouth cavity between a central bottom surface of the tongue and the musculature at the bottom of the mouth with a surface which contacts the tongue for lifting the tongue upward toward the mouth cavity. The displacement member cooperates with a mouthpiece-shaped element that can be placed between the teeth of the upper and lower jaw. The mouthpiece-shaped element provides at least one through-hole for ventilation of the mouth cavity with air that is breathed.

In a preferred embodiment, the displacement member of the invention is spherical and, with regard to shape and size, is largely adapted to the geometric conditions of the intraoral anatomy of a person in such a way that when the device is inserted orally, the spherical displacement member is placed beneath the central portion of the tongue between the bottom of the tongue and the musculature at the bottom of the mouth. The tongue is pressed in toward and upward toward the palate without producing an unpleasant feeling of displacement in the mouth for the person concerned. The ball diameter of the spherical displacement member should therefore be between 1.5 and 2 cm. The arrangement of the spherical element at the middle of the lower surface of the tongue supports the drooping tongue muscles and draws them toward the teeth, thus opening the airway.

In a further preferred embodiment the displacement member is configured as two spherical elements in which the ball geometries penetrate one another locally in part. A displacement member configured in this manner is positioned orally in such a way that in each case a spherical element respectively comes to rest to the right and left of the frenulum of the tongue at a central location in contact with an under surface of the tongue.

The displacement member is preferably rigidly connected via a connection portion to the mouthpiece-shaped element, which has a curved, elongate, strand-like shape comprising an upper and lower biting surface onto which the front teeth can bite. Preferably the teeth of the upper and lower jaw are delimited laterally by the canines. The connection is symmetrically disposed about a center line of the mouthpiece and the surface comprises either a spherical surface of comprises two intersecting spherical surfaces respectively disposed to a right and to a left of the frenulum of the tongue.

The mouthpiece-shaped element is penetrated by at least one and preferably, by numerous through-holes for the purpose of providing an unimpeded supply of air for breathing by the person. In order to make the wearing comfort of the device according to the invention as agreeable as possible for the person, the mouthpiece-shaped element should not exceed a discernible thickness of 2 cm during biting.

In a further configuration of the device according to the invention, the mouthpiece-shaped element or the displacement member is connected via an adjustable tensioning device retained at the ears, in such a way that the tongue is pressed toward the palate in a clear position during sleep. The tensioning device includes a band-like, flexible material and should comprise means for adjusting its length.

The shape and size of the spherical elements and the mouthpiece-shaped element are important for wearing comfort and must be adapted to the respective shape and size of the person's airways. This also applies to the configuration of the tensioning device, which comprises means for hanging over the ears. All materials used to form the device according to the invention must be resistant to oral fluids and physiologically safe.

In specific cases, in order to assist the anti-snoring device being worn orally, it is expedient to insert a resilient moulded plug that comprises a through-hole and is held in the ala of the nose by resilient tension in order to hold the ala of the nose open. This measure ensures that the airway is held open via the nasal cavities and the air flowing in is controlled.

BRIEF DESCRIPTION OF THE DRAWINGS

The invention will be described hereinafter by way of example, by means of embodiments with no limitation to the general concept of the invention and with reference to the drawings, in which:

FIGS. 4 *a-e* are views of a first embodiment from various sides; and

DESCRIPTION OF EMBODIMENTS OF THE INVENTION

Figure 1:
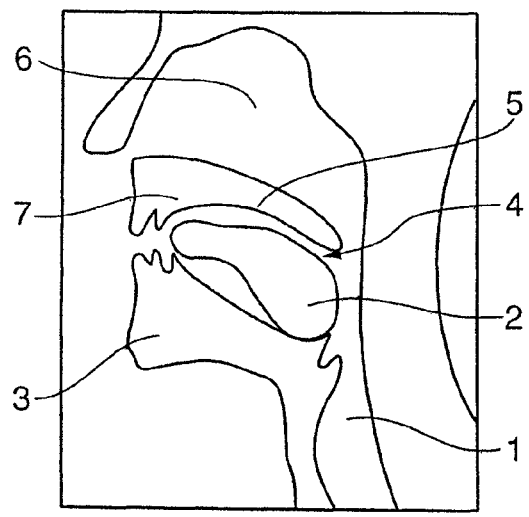
FIG. 1 is an illustration of free airways.

FIG. 1 shows a schematic view of a section through the human airways. Air is guided through the nasal cavities 6 and the mouth cavity 4 into the windpipe 1. It is important that the entrance to the windpipe 1 is not constricted, either completely or in part, by the tongue 2 or the soft palate. The entry of air between the tongue 2 and the soft palate 5 must also be maintained. FIG. 1 also shows the lower jaw 3 which is displaced in toward the windpipe during snoring.

Figure 2:
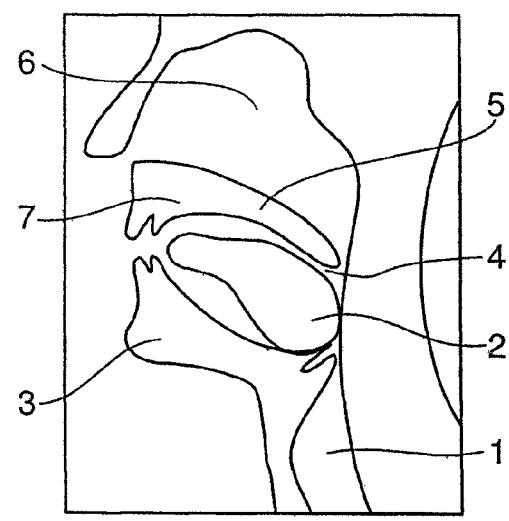
FIG. 2 is an illustration of closed airways in the case of obstructive apnoea.

FIG. 2 shows (schematically) the situation when the airways are closed, which leads to snoring, although a partial closure can also trigger snoring (not shown). In this situation, the tongue 2 is pushed rearwards by the drooping tongue muscles and closes the airway through the windpipe 1, at least intermittently.

The device according to the invention may help to avoid this situation. The device according to the invention lifts the tongue muscles at a central location, which droop during sleeping, in toward the mouth cavity, resulting in the windpipe not being closed completely. The central part of the lower surface of the tongue is drawn to the base of the mouth cavity and fixed forwards by a fold in the oral mucosa (the frenulum of the tongue) in such a way that only the tip and lateral edges are free.

Figure 3:
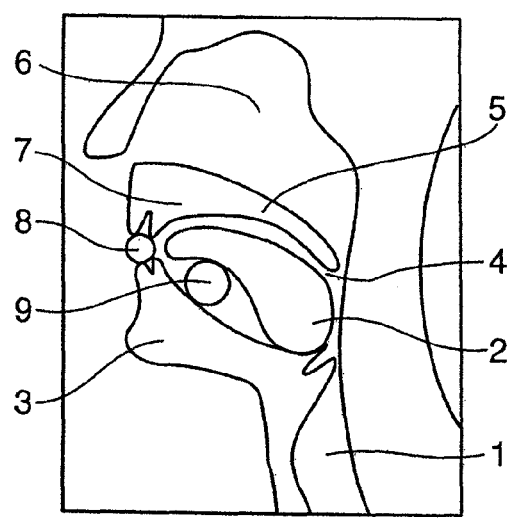
FIG. 3 is a schematic view of the operating principle of the anti-snoring device according to the invention.

As shown in FIG. 3, a single spherical element 9 is placed at the lower surface of the tongue 2 in the central region next to the frenulum of the tongue whereas the anti-snoring device of FIG. 5 has two spherical elements 9, so that a spherical element 9 is placed in each case to the right and left of the frenulum of the tongue. The spherical elements have a diameter of 1.5 to 2.0 cm which in each case depend on the shape and size of the wearer's tongue. Each spherical element 8 is placed between the bottom of the tongue and the musculature at the bottom of the mouth and has a surface for lifting the tongue upward in toward the soft palate 5 of the mouth cavity.

The spherical elements Q are connected to a mouthpiece-shaped element 8 via a connection means. The mouthpiece-shaped element lies between the teeth when the spherical elements 9 or 91 and 92 have been brought into their intended position. The mouthpiece-shaped element 8 has at least one cross-hole with a diameter of 2.5 to 3.5 mm so air can flow through for breathing.

If needed, two or more holes can also be provided. The mouthpiece-shaped element 8 also enlarges the mouth cavity 4 in such a way that the entire mouth cavity has more air space.

The oral part of the anti-snoring device therefore has two interconnected parts which are the spherical element 9 of elements 91 and 92 lying beneath the tongue and the mouthpiece-shaped element 8 lying between the teeth of the upper and lower jaw.

Since the mouthpiece-shaped element 8, as described above, creates more air space, in some cases it should also be ensured that the nasal opening is controlled in such a way that breathing does not result in too much air being inhaled. All of the air that is breathed is balanced in this instance. Resilient moulded parts comprising through-holes that are inserted under tension into the nasal cavities are used for this purpose. These moulded parts have a length of approx. 2 cm-3 cm and a diameter of 1.0 to 1.5 cm. In the idle state, the lower face of the moulded parts is flat and the upper face is curved. Before use, the moulded part is slightly rolled together in such a way that it can be inserted into the nasal opening. The moulded parts are used in pairs so it is expedient to connect them. The connection member may also be used as a tensioning element that presses the moulded parts against the inner nasal wall.

The spherical elements 9 or 91 and 92 can optionally be interconnected via an adjustable tensioning device (not shown). Each end of the tensioning device is equipped with an eye that is pulled over each auricle to provide retention. The eyes can be enlarged if required. The tensioning device generally has a resilient strap that must be resistant to oral fluid and physiologically safe. The spherical element 9 or the two spherical elements 91 and 92 are threaded onto the tensioning device and fixed thereto in case of emergency. The spherical elements 9 or 91 and 92 therefore comprise a central hole. The contact pressure of each spherical element 9 or 91 and 92 from beneath the tongue can be increased using the tensioning device fixed at the ear.

The representations according to FIGS. 4a to e show perspective views of a preferred anti-snoring device, to which reference is made below.

The spherical displacement member 9 is rigidly connected to the concave side of the longitudinally curved, mouthpiece-shaped element 8 via a connection portion 14. The anti-snoring device illustrated in FIGS. 4a to e is formed in one piece and uses a biocompatible plastics material that remains firm under biting.

The mouthpiece-shaped element 8 comprises an upper and lower biting surface 10 and 11, onto which the front teeth in particular of the upper and lower jaw, each preferably defined laterally by the bite of the canines. The mouthpiece-shaped element 8 thus has a curved length L typically between 3 and 4 cm. depending on the oral anatomy of a person. In order to avoid overbiting and to assist with the intraoral self-centering positioning of the anti-snoring device inside the mouth cavity, the two bite surfaces 10 and 11 are defined at least by a front defining edge 12 that rises preferably perpendicularly over the respective bite surfaces 10 and 11. Not necessarily but in an advantageous configuration, the bite surfaces 10 and 11 are also defined rearwardly by a corresponding defining edge 13.

The 'thickness' of the mouthpiece-shaped element 8 that determines the jaw opening is determined by the orthogonal distance d between the two defining surfaces 10 and 11, which is at least 5 mm. but should not exceed 2 cm.

In order to supply the person with sufficient air to breathe through the mouth cavity, the mouthpiece-shaped element 8 provides a number of channel-like through-holes 15, typically with opening cross-sections between 2.5 and 3.5 mm. The number and arrangement of the through-holes 15 are also adaptable depending on the breathing behaviour of the person concerned.

Owing to the longitudinally curved shaping of the mouthpiece-shaped element 8 adapted to the natural bite surface of the teeth of the upper and lower jaw, the mouthpiece-shaped element comprises a concave inner face to which the spherical displacement member 9 or members 91 and 92 is attached respectively via a connection portion 14 or 14'. The length of the connection portion 14 and 14' separating the spherical displacement member 9 or 91 and 92 from the mouthpiece-shaped element 8 is selected so that when the anti-snoring device is positioned orally, the spherical displacement member 9 or members 91 and 92 lies between the tongue and the musculature at the bottom of the mouth directly adjacent to the frenulum of the tongue. The spherical displacement member 9 or members 91 and 92 attach relative to the mouthpiece-shaped element 8 respectively by the connection portion 14 or 14' in such a way that the spherical displacement members are positioned in the recessed, lower region of the musculature at the bottom of the mouth relative to the teeth of the lower jaw. The ball center point M of the spherical displacement member 9 or members 91 and 92 are located beneath a central plane A that extends centrally between the two bite surfaces 10 and 11. In the embodiment shown, the spatial position of the ball center point M is arranged in the plane of the lower bite surface 11 of the mouthpiece-shaped element 8 as shown in FIG. 4c.

Figure 5A:
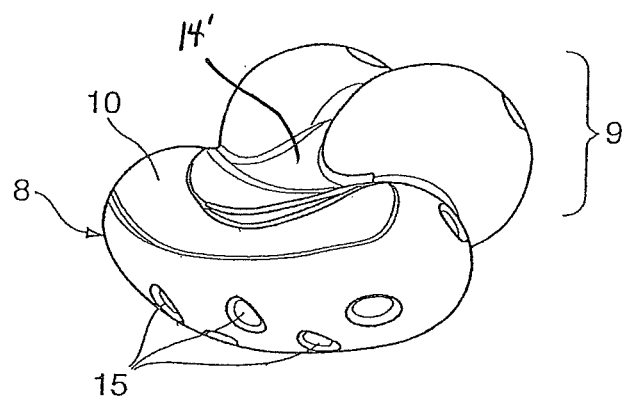
FIGS. 5 *a-c* are views of a second embodiment from various sides.
Figure 5B:
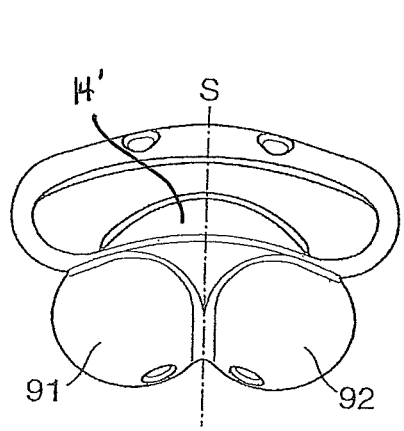
Figure 5C:
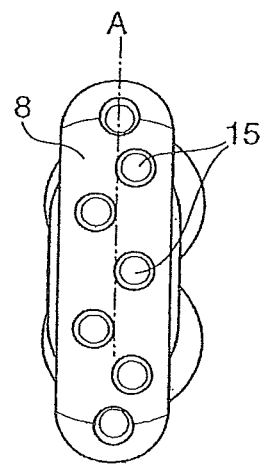

A further embodiment is illustrated in FIGS. 5a to c, which also shows three-dimensional views from different viewing angles of the same embodiment. In contrast to the embodiment described above in FIG. 4, the embodiment illustrated in FIGS. 5a to 5c comprises two spherical elements 91 and 92 that, together, constitute the displacement member 9. The mouthpiece-shaped element 8 is largely identical to that in the embodiment according to FIG. 4. The spherical elements 91 and 92 are nestled symmetrically about the axis of symmetry S indicated in FIG. 5b and practically seamlessly against the mouthpiece-shaped element 8. The spherical elements 91 and 92 are placed in each case to the left and right of the frenulum of the tongue when positioned orally, in such a way that the frenulum of the tongue comes to lie approximately along the axis of symmetry S indicated in FIG. 5b. Even if the anti-snoring device according to FIGS. 5a to 5c becomes trapped, the spherical elements 91 and 92 are slightly lowered relative to the central plane A described above as shown in FIG. 5c in such a way that the spherical elements 91 and 92 are positioned within the region of the musculature at the bottom of the mouth.

All the surfaces of the anti-snoring device configured according to the invention are smooth and rounded in such a way that there is no risk of injury within the mouth cavity. In order to improve the wearing comfort for a person, the biocompatible plastics material that remains firm under biting should be as light as possible. The anti-snoring device according to the invention also enables cost-effective production, for example by an injection moulding method.

LIST OF REFERENCE NUMERALS 1 windpipe
2 tongue
3 lower jaw
4 mouth cavity
5 soft palate
6 nasal cavity
7 upper jaw
8 mouthpiece-shaped element
9 displacement member and element
91 and 92 spherical elements
10 upper bite surface
11 lower bite surface
12 front defining edge
13 rear defining edge
14 connection portion
14' connection portion
15 through-hole
M ball center point
L curved length of the mouthpiece-shaped element
A central plane
d distance between the bite surfaces
S axis of symmetry

The invention claimed is:

1. An anti-snoring device adapted for insertion into an oral mouth cavity of a person, comprising:
   a mouthpiece adapted to extend inward into the mouth cavity from teeth of the person and including at least one through-hole for ventilation of the mouth cavity during breathing; and
   means for counteracting snoring including a displacement member which is shaped, sized and adapted for placement within the mouth cavity which is adapted to contacts a central bottom surface of a tongue of the person and is adapted to contact musculature of the person at the bottom of the mouth cavity, the displacement member including a surface, adapted to be positioned in the mouth cavity, that lifts the central bottom surface of the tongue upward toward a palate of the mouth cavity to counteract snoring, the surface while disposed in the mouth cavity being symmetrically disposed about a center line of the displacement member which is adapted to pass through a frenulum of the tongue while the device is in the mouth cavity; and a connection which connects the displacement member to the mouthpiece and which is also adapted to be symmetrically disposed about the center line and the surface comprises either a spherical surface or comprises two intersecting spherical surfaces adapted to be disposed to a right and to a left of the frenulum of the tongue.

2. The anti-snoring device according to claim 1, wherein the surface is has a diameter between 1.5 and 2.0 cm.

3. The anti-snoring device according to claim 2, wherein the displacement member and the mouthpiece are rigidly joined by the connection.

4. The anti-snoring device according to claim 3, wherein the displacement member is connected by the connection to a concave side of the mouthpiece.

5. The anti-snoring device according to claim 2, wherein the mouthpiece is longitudinally curved and has upper and lower separated bite surfaces, between which the at least one through-hole extends providing an air passage during breathing, which extends along a longitudinal portion of the mouthpiece.

6. The anti-snoring device according to claim 2, wherein the displacement member is connected by the connection to a concave side of the mouthpiece.

7. The anti-snoring device according to claim 1, wherein each has a diameter between 1.5 and 2.0 cm.

8. The anti-snoring device according to claim 7, wherein the displacement member and the mouthpiece are rigidly joined by the connection.

9. The anti-snoring device according to claim 8, wherein the displacement member is connected by the connection to a concave side of the mouthpiece.

10. The anti-snoring device according to claim 7, wherein the mouthpiece is longitudinally curved and has upper and lower separated bite surfaces, between which the at least one through-hole extends providing an air passage during breathing, which extends along a longitudinal portion of the mouthpiece.

11. The anti-snoring device according to claim 7, wherein the displacement member is connected by the connection to a concave side of the mouthpiece.

12. The anti-snoring device according to claim 1, wherein the mouthpiece is longitudinally curved and has with upper and lower separated bite surfaces, between which the at least one through-hole extends providing an air passage for breathing, which extends along a longitudinal portion of the mouthpiece.

13. The anti-snoring device according to claim 12, wherein the upper and lower bite surfaces each include an edge which is longitudinal relative to a curved longitudinal extension of the mouthpiece and against which an edge of front surfaces of teeth of an upper and lower jaw of the person are adapted to contact.

14. The anti-snoring device according to claim 1, comprising a center point of the spherical surface which projects parallel to at least one bite surface outside a central plane displaced between upper and lower bite surfaces.

15. The anti-snoring device according to claim 14, wherein the center point projects toward at least one bite surface which is closer to the lower bite surface than to the upper bite surface.

16. The anti-snoring device according to claim 1, comprising center points of the spherical surfaces which project parallel to at least one bite surface outside a central plane displaced between upper and lower bite surfaces.

17. The anti-snoring device according to claim 16, wherein the center points project toward at least one bite surface which is closer to the lower bite surface than to the upper bite surface.

18. The anti-snoring device according to claim 1, wherein the displacement member is connected by the connection to a concave side of the mouthpiece.

19. The anti-snoring device according to claim 1, wherein the mouthpiece has a curved length of 3 to 4 cm and the at least one through-hole comprises an opening having a cross-section of 2.5 to 3.5 mm.

20. The anti-snoring device according to claim 1, wherein the mouthpiece is connected via an adjustable tensioning device which is adapted to be retained at ears of the person so that the tongue is pressed in toward a palate of the person during sleep.

21. The anti-snoring device according to claim 1, wherein the displacement member is connected via the connection to a concave side of the mouthpiece.

* * * * *